(12) United States Patent
Zipprich et al.

(10) Patent No.: US 8,597,023 B2
(45) Date of Patent: Dec. 3, 2013

(54) DENTAL IMPLANT AND METHOD FOR PROVIDING A MOUNTING PART

(75) Inventors: Holger Zipprich, Darmstadt (DE); Andreas Witt, Niedenstein (DE)

(73) Assignee: SIC Invent AG, Basel (CH)

( * ) Notice: Subject to any disclaimer, the term of this patent is extended or adjusted under 35 U.S.C. 154(b) by 156 days.

(21) Appl. No.: 12/665,598

(22) PCT Filed: Jun. 23, 2008

(86) PCT No.: PCT/EP2008/005049
§ 371 (c)(1),
(2), (4) Date: Apr. 12, 2010

(87) PCT Pub. No.: WO2008/155135
PCT Pub. Date: Dec. 24, 2008

(65) Prior Publication Data
US 2010/0196853 A1    Aug. 5, 2010

(30) Foreign Application Priority Data
Jun. 21, 2007  (EP) .................................... 07012136

(51) Int. Cl.
*A61C 8/00*    (2006.01)
(52) U.S. Cl.
USPC .......................................... 433/173; 433/174

(58) Field of Classification Search
USPC ...................... 433/172–176, 201.1; 606/290, 606/278–279, 269; 623/17.17
See application file for complete search history.

(56) References Cited

U.S. PATENT DOCUMENTS

| 5,674,072 A | 10/1997 | Moser et al. |
| 2008/0182227 A1* | 7/2008 | Wolf et al. ..................... 433/174 |

FOREIGN PATENT DOCUMENTS

| DE | 101 29 684 | 1/2003 |
| DE | 10 2005 005 402 | 8/2006 |
| EP | 0 707 835 | 4/1996 |
| FR | 2785788 A1 * | 5/2000 |

OTHER PUBLICATIONS

International Search Report for PCT/EP2008/005049 mailed Oct. 21, 2008.

* cited by examiner

*Primary Examiner* — Yogesh Patel
(74) *Attorney, Agent, or Firm* — Suzannah K. Sundby, Esq.; Smith, Gambrell & Russell, LLP (57) ABSTRACT

Disclosed herein is a dental implant with a post part which can be introduced into a jaw bone and with a mounting part on which a dental prosthesis piece can be mounted. The dental implant allows a dental technician to choose a particularly favorable orientation for further assembling of the components, and at the same time to make it possible for the person performing the treatment to make use of the advantages of an indexing without using auxiliary tools.

7 Claims, 9 Drawing Sheets

FIG. 1

-- PRIOR ART --

FIG. 2

-- PRIOR ART --

FIG. 3

-- PRIOR ART --

FIG. 4

-- PRIOR ART --

FIG. 5

-- PRIOR ART --

DENTAL IMPLANT AND METHOD FOR PROVIDING A MOUNTING PART

This application is a 371 National Phase of PCT/EP2008/005049, filed 23 Jun. 2008, and claims foreign priority to EP 07012136.3, filed 21 Jun. 2007.

The invention relates to a dental implant with a post part which can be introduced into a jaw bone and with a mounting part assigned to this, on to which a dental prosthesis piece can be mounted.

Dental implants are known in various forms. They are usually inserted by screwing into the jaw bone in place of a tooth which has been extracted or has fallen out, in order to hold there, after a healing in phase of from three to four months, a prosthetic mounting part which serves as a dental prosthesis, or a crown. For this, such a dental implant is conventionally constructed as a suitably shaped metal body and is shaped in the manner of a pin, and has at the apical end a usually self-tapping screw thread with which the pin can be inserted into the appropriately prepared implant bed.

Figure 1:
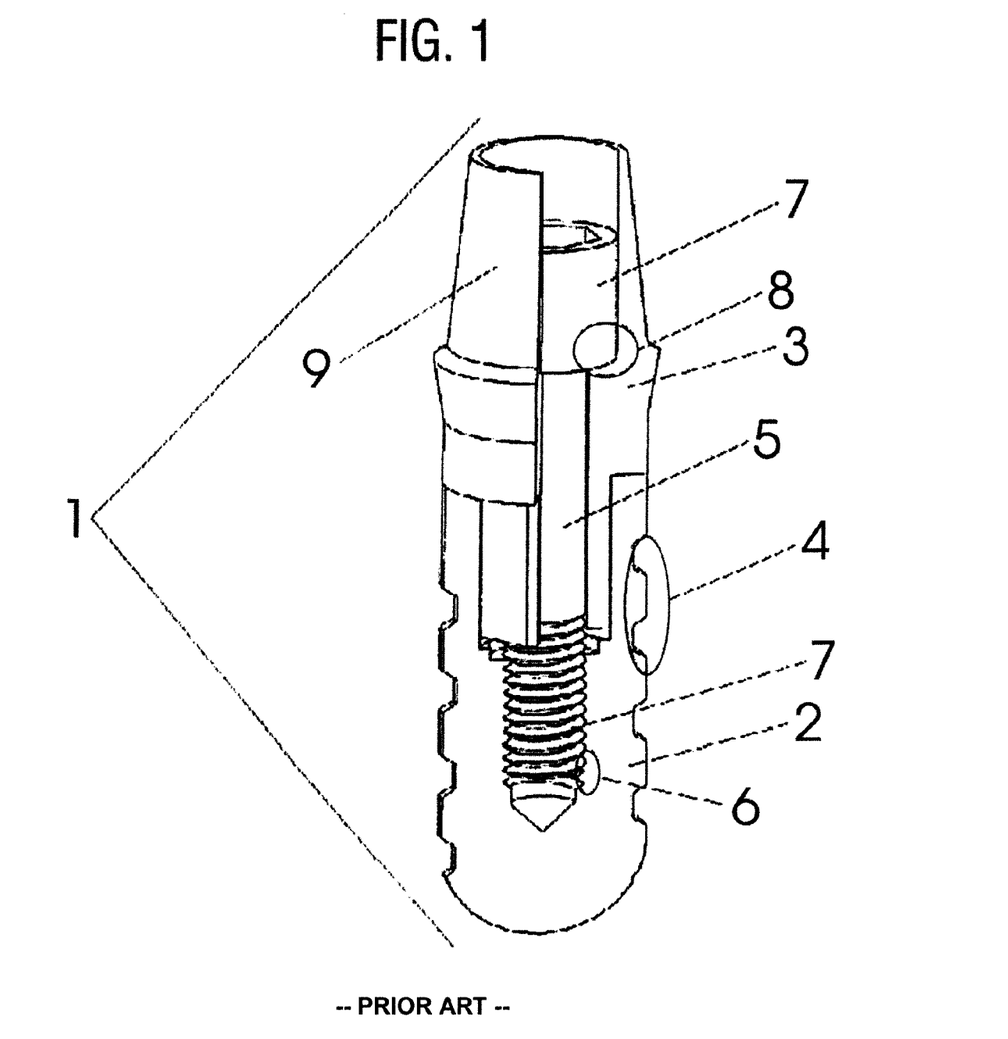
FIGS. 1 to 5 each show a dental implant according to the prior art.
Figure 2:
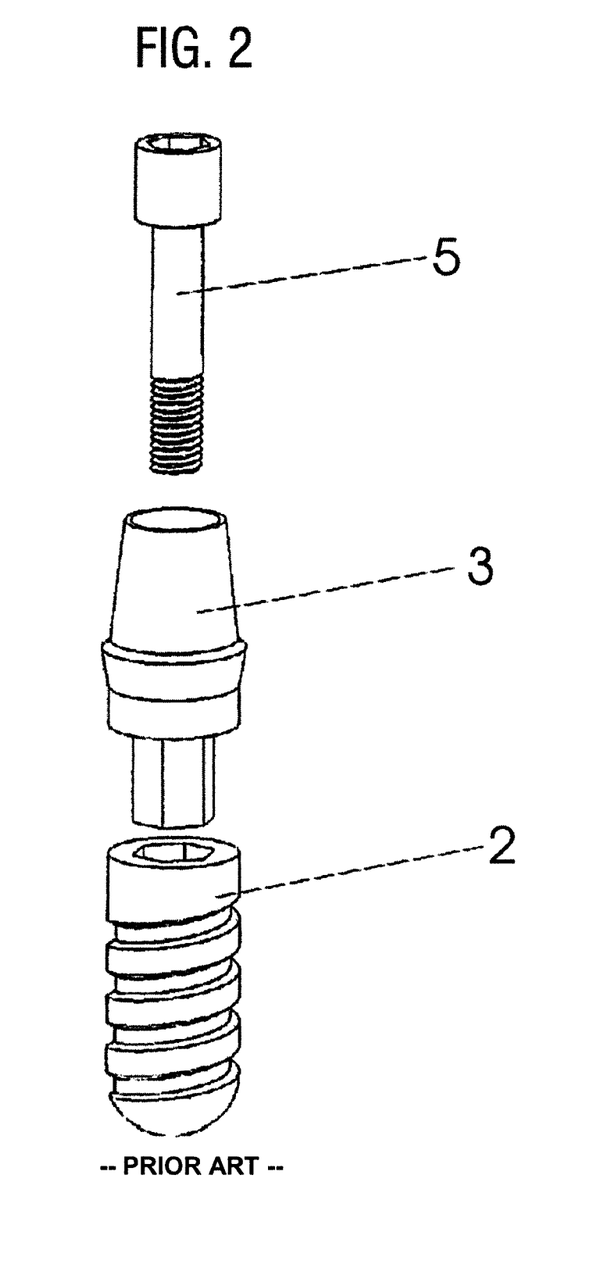

An example of a dental implant of the abovementioned type is shown in FIG. 1 in a partial view and partially in an axial section and in FIG. 2 as an exploded drawing. The two-part dental implant 1 comprises a post part 2 and a mounting part 3. The post part 2, like the head or mounting part 3, is made of metal or a ceramic, and indeed in particular of titanium, a titanium alloy, a titanium-containing alloy, a zirconium oxide or aluminium oxide ceramic or a ceramic which contains either zirconium oxide or aluminium oxide. The post part 2 is provided externally with a thread 4, which can be configured as a self-tapping thread or as a thread which is not self-tapping. The pitch of the thread can be uniform or variable in configuration. The outer form of the post part 2 can also be configured without a thread, with and without mechanical retention aids. The post part 2 and the mounting part 3 are screwed to one another via a connecting screw 5. For this, the thread of the connecting screw 5 is screwed into an internal thread 6 of the post part 2. When the connecting screw 5 is screwed in, the screw head 7 of the connecting screw 5 presses the mounting part 3 on to the post part 2 via the front indentation 8 of the mounting part 3.

The post part 2 is anchored in an appropriately prepared implant bed of the jaw bone. The thread construction here ensures a high primary stability and a uniform transmission of the forces which arise during chewing into the jaw bone. The mounting part 3 is connected in its upper region 9 to a crown, another prosthetic care item, or the like (not shown) in a manner known per se.

This connection can be configured as screwing, clamping, conical self-locking, vacuum. magnet, ball-head system, cementing, gluing or the like.

In order to counteract rotation or twisting between the mounting part 3 and the post part 2 due to external forces (usually caused by chewing), either mechanical indexing in the form of a mechanical barrier is used, or the surface pressure between the mounting part 3 and the post part 2 is suitably chosen.

Figure 3:
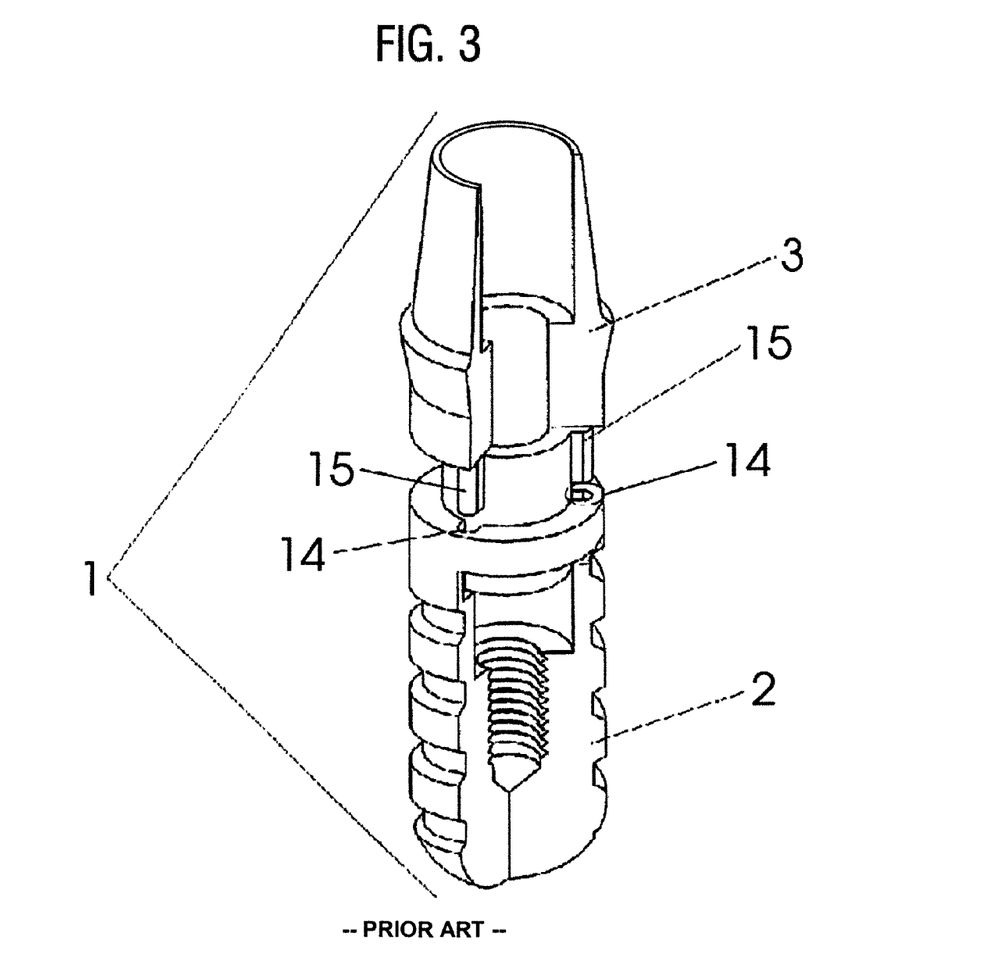

The mechanical barrier used for indexing and for avoiding rotation of the mounting part 3 on the post part 2 can be configured in various variants. For this, in the example according to FIGS. 1 and 2 a hexagon socket is provided in the post part 2 and a hexagon insert is provided on the mounting part 3, it also being possible for the configuration as hexagon insert and socket to be the reverse. The number of edges of such an edge system can vary. Furthermore, the corners of such edge systems can be provided with a radius. Torx and polygon systems with a varying number of elements and varying geometry are known as further embodiments. In an alternative embodiment, as shown in FIG. 3, indexings by means of milled cuts 14 in the post part 2 and projecting elements 15 or cams on the mounting part 3 are moreover known.

Figure 4:
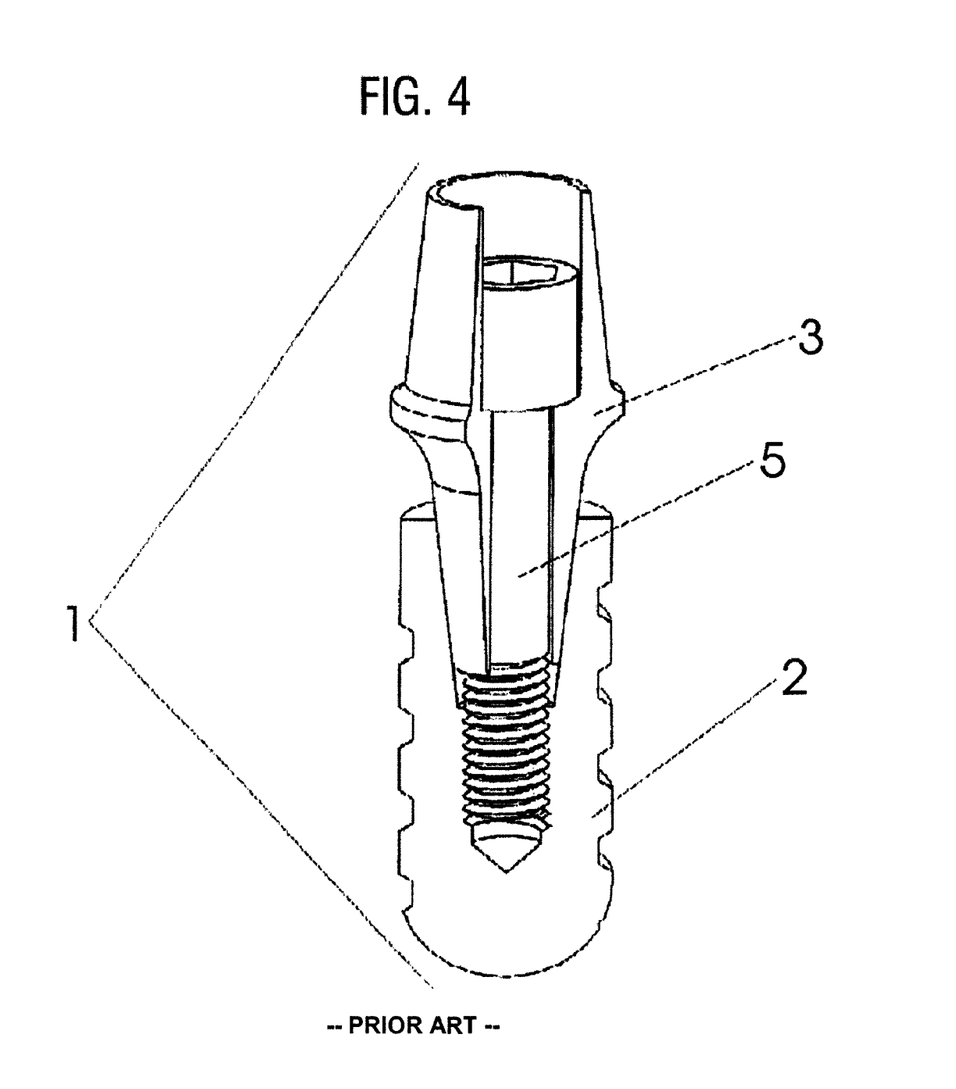

Rotation between the post part 2 and the mounting part 3 is avoided here via the pressing force of the connecting screw. In addition or alternatively, the connection between the post part 2 and the mounting part 3 can be configured mostly conically. In particular, these are embodiments of the type shown in FIG. 4, which are configured as a conical catch or conical self-locking catch on the basis of the taper and the surface friction between the conical contact surfaces of the post part 2 and the mounting part 3 when the connecting screw 5 is tightened via the conical contact points between the post part 2 and the mounting part 3.

Figure 5:
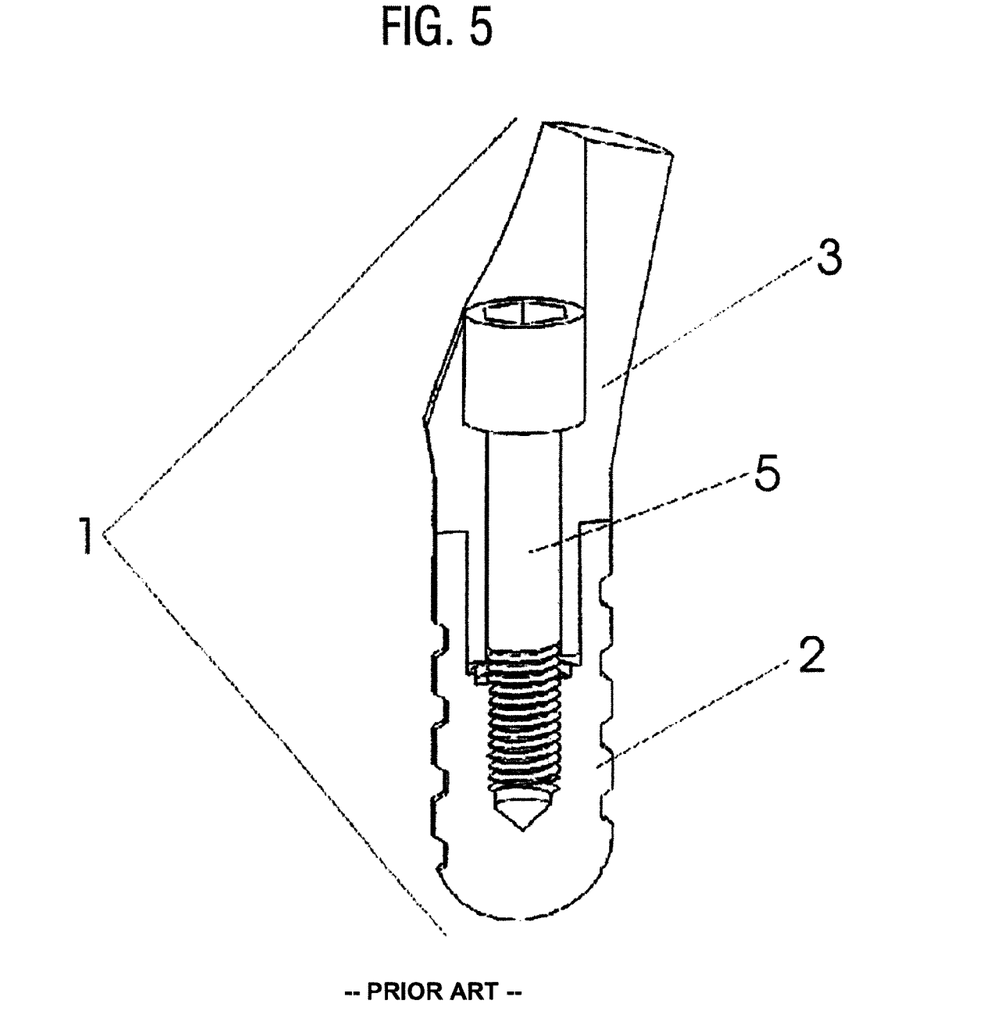

Depending on the insertion position (front teeth or back teeth region, lower jaw, upper jaw), the bone substance, the remaining teeth, the course and position of the vessels and nerves, the person performing the treatment is not always able to drill the bore for the post part/implant to coincide with the axis of the prosthetic care item (crown or the like). It follows from this that a post part/implant of straight configuration and a mounting part of straight configuration do not meet the anatomical circumstances of the patient. To counteract this problem, angled mounting parts are used (FIG. 5). Angled mounting parts are also called angulated mounting parts. FIG. 5 shows a dental implant 1 with a post part 2 and an angled/angulated mounting part 3, wherein the post part 2 and the angulated mounting part 3 are screwed to one another via the connecting screw 5.

This angle is conventionally between 10° and 30°. After the insertion, preferably after the healing in of the post parts, the spatial and geometric information of the remaining teeth (e.g. antagonists, teeth mesially and distally from the insertion position), the mucous membrane and the post part/implant or the assembled mounting part must be determined for production of the crown, bridge or the like. This spatial and geometric information is necessary in order to produce the crown, bridge or the like in an exact fit and in an anatomically optimized manner. For this purpose, an impression, preferably of silicone or another dental impression material, of the situation in the mouth is produced. A cast is preferably made from this impression with gypsum or another dental modelling material. This gypsum model is a duplicate of the situation in the patient's mouth. It provides the dentist or the dental technician with information about the position of the remaining teeth, the mucous membrane and the post parts/implant inserted.

To improve the transfer of the position and geometry of the post parts/implants inserted, special impression posts of metal and/or plastic are preferably pushed and/or screwed on to the post part/implant inserted. The impression is then produced in the mouth, preferably with silicone. After curing of the impression material, when the impression is removed the impression posts either remain on the implant or are removed with the impression. When the cast is made from the impression, the impression posts/mounting posts must be placed in the impression and connected to a laboratory implant. This laboratory implant has the same or a similar geometric form to the inserted post part/implant with respect to the connection and geometrically in the direction of the impression post/mounting post. After the cast has been made from the impression with the integrated impression posts/mounting posts and integrated laboratory implant, a gypsum model with the embedded laboratory implant is obtained.

If the implant system used has indexing, this has been transferred from the patient's mouth to the gypsum model. The prosthetic care item of the implant/implants is planned and produced on the basis of this gypsum model. The rotatory position of the mounting part on the implant plays a decisive role here. If the implant system used has indexing, the positioning possibilities of the mounting part on the laboratory implant are limited. In the case of a hexagon connection, there are six positioning possibilities. In the case of an implant system without indexing, all positions between 0° and 360° can be used. After production, a trial in the patient's mouth is usually undertaken. During this trial or the final integration of the dental prosthesis, the person performing the treatment must integrate the mounting part/the mounting parts and all other prosthetic elements in the patient's mouth in the same position as on the gypsum model.

If the implant system inserted is equipped with indexing, the person performing the treatment has a limited number of possible choices for determining the desired position. If no indexing exists with the implant system used, the person performing the treatment cannot use the advantage of limited positioning to determine the desired position. The person performing the treatment must determine the information about the desired rotatory position(s) of the mounting part(s) on the implant(s) another way. For this, individual keys are usually produced by the dental technician. The individual key is assembled on the mounting parts/the mounting part and placed as a whole on the implants with the aid of the adjacent teeth and/or the adjacent anatomical structure. After the mounting parts have been fixed on the implants (screwing, cementing etc.), the individual key can be removed and the remaining integration of the prosthetic components can take place. In conclusion, it can be said that for optimized production of the prosthetic components it is advantageous if the dental technician is not limited in the choice of the rotatory positioning by indexing in the connection of the mounting part and the implant. If an individual key has to be produced, however, for the dental technician this is associated with outlay and costs. Furthermore, for the person performing the treatment the integration is associated with a higher outlay. For the dentist, it is more favourable if the number of positioning possibilities of the mounting part on the implant is as low as possible. Eight to twelve possibilities are acceptable, advantageously 3-5 possibilities, but in particular 1-2 positioning possibilities.

It is therefore desirable for the dental technician to be able to use an infinitely variable rotatory freedom of movement of the angulated or non-angulated mounting part/parts of 360°, but for the dentist, without an aid for integration of the one-part or multi-part mounting part in the manner of indexing, to have only a small number of positioning possibilities on the post part in the patient's mouth, so that expensive alignment and positioning during the actual treatment, that is to say in the patient's mouth, can be omitted.

The invention is therefore based on the object of providing a dental implant of the abovementioned type and a method for providing a mounting part of a dental implant which allows the dental technician, with an overall risk of infection which is kept low, to use all the positions between 0° and 360°, and at the same time makes it possible for the person performing the treatment to make use of the advantages of indexing which are described above without using auxiliary tools (e.g. individual keys).

With respect to the dental implant, this object is achieved according to the invention by the features of claim 1. It is proposed here that the dental implant has a mounting part which is configured in at least two parts and connects the post part implanted in the jaw bone with the dental prosthesis part. The mounting part here comprises on the one hand a first mounting part piece which, when viewed in the longitudinal direction of the post part, can be pushed into a receiving channel arranged in this, and on the other hand a second mounting part piece for assembling the dental prosthesis piece. The first and the second mounting part piece here can be brought into contact with one another in a contact region in which both components have an essentially circular cross-section, whereas the internal contour of the receiving channel, like the external contour of the first mounting part piece tailored thereto, has a multi-membered symmetry.

By means of this construction, after suitable determination of the desired orientation or rotatory alignment of the construction initially in the laboratory, that is to say, for example, by the dental technician, the fine adjustment or rotatory alignment can be carried out by suitable twisting between the first and second mounting part piece. Due to the circular cross-sections of the components in the corresponding contact region, an essentially free twistability of these components with respect to one another is ensured here, so that any desired orientation can be established. The mounting part pieces correctly aligned in such a manner can then be suitably fixed to one another while still in the laboratory and therefore outside the patient's mouth, so that the orientation already established is also retained for the further working steps. In a later working step, in particular by the dentist, the entire mounting part is then connected to the post part already implanted in the jaw bone, the first mounting part piece being pushed into the assigned receiving channel in the post part. Due to the multi-membered symmetry of the cross-section of the receiving channel and of the assigned segment of the first mounting part, it is ensured here that only a small number of orientations is possible during this pushing in, so that the correct alignment is ensured with a fine adjustment rapidly and without a great outlay. The treatment phase in the patient's mouth can therefore be kept particularly short.

By the multi-part configuration of the mounting part, decoupling of a freely choosable rotation with respect to the final alignment of the longitudinal direction of the mounting part assembling region provided for assembling the crown or the dental prosthesis by the dental technician on the one hand, from a direction requirement of the intermediate product, once prefabricated, for final mounting of the mounting part on the post part already implanted in the patient's mouth by the dentist on the other hand is therefore made possible. With full utilization of the resulting freedom of rotation between the two mounting part pieces, the dental technician can therefore carry out an alignment of the components under circumstances which are optimized for him. The mounting part pieces are then fixed to one another, so that the alignment carried out by the dental technician is retained. During the final mounting on the post part in the patient's mouth, which is possible in only one given orientation because of the positive-locking fit of the contact pin provided there to the assigned formed recess, the dentist can then produce the finished dental implant with the envisaged alignment without noticeable outlay on adjustment.

The dental implant is moreover designed with the aim of preventing or at least limiting penetration of bacteria, contamination or the like into the region of the mechanical contact points of the individual mounting part pieces. For this, the second mounting part piece is configured by suitable shaping such that with the assembled dental implant in cooperation with the post part, an encapsulation or covering which surrounds the first mounting part piece and the receiving channel assigned to this results. For formation of this capsule or cover, the first mounting part piece has a contact surface which comes into contact with a corresponding contact surface of the post part when the mounting part is mounted on the posts. For a particularly effective tightness of this contacting, which is provided for formation of the desired encapsulation, these contact surfaces are suitably configured conically to correspond to one another, so that during assembling of the mounting part by suitable pressing in of the cone, viewed in the longitudinal direction of the post part, the desired tight contact arises. For this, the second mounting part piece is provided with a peripheral sealing collar with an essentially conical outer surface, which can be brought into contact with a corresponding inner surface of the post part to form the capsule. A particularly high tightness can be achieved here by this inner surface of the post part in turn likewise being conical in configuration.

The desired merely limited number of possible orientations during introduction of the mounting part into the post part can be achieved in an advantageous embodiment by the internal contour of the receiving channel having a three-membered symmetry in cross-section The desired multi-membered symmetry of the internal contour of the receiving channel and, tailored to this, of the external contour in the corresponding region of the first mounting part piece can be achieved in a particularly simple manner in an advantageous embodiment by the internal contour of the receiving channel being configured in cross-section essentially as a polygon, preferably as a hexagon. In an alternative advantageous embodiment, the internal contour of the receiving channel is configured essentially circular in cross-section, complemented by a number of moulded-on cams.

With respect to the method for providing a mounting part of a dental implant, the object mentioned is achieved according to the invention by the first mounting part piece being fixed securely against twisting on the second mounting part piece before the second mounting part piece is inserted into the post part of the dental implant. Only by fixing the two mounting part pieces securely against twisting is the dental technician or dentist in the position in fact to align and to work the second mounting part piece accordingly in the laboratory.

The functional progress of introduction of the dental prosthesis breaks down as follows:

The steps after insertion of the post part up to production of the model, preferably from gypsum, remain as described above. The dental technician/dentist can now choose a rotatory position of the secondary mounting part on the primary mounting part which is optimum for the form of the prosthesis. When the dental technician/dentist has found the optimum position of the secondary mounting part on the primary mounting part, he can fix this position. This means that after fixing of the individual elements of the multi-part mounting part, the remaining prosthetic components can be produced without one of the elements of the multi-part mounting part becoming displaced in a rotatory and/or translatory manner with respect to one of the other elements of the multi-part mounting part. The fixing consequently prevents and/or impedes the rotatory and/or the translatory freedom of movement of the individual elements of the multi-part mounting part with respect to one another. After production of the prosthetic components, the person performing the treatment obtains the multi-part and internally fixed mounting part and the remaining prosthetic components. In the patient's mouth, the person performing the treatment can make use of the indexing between the post part and the multi-part mounting part given by the multi-membered symmetry of the receiving channel and the corresponding segment of the first mounting part.

With the indexing, the person performing the treatment can otherwise easily determine the desired rotatory position of the multi-part mounting part and integrate the multi-part mounting part as a whole. This can be effected by means of a connecting screw, a catch (preferably a conical self-locking catch), a locking mechanism, a latch mechanism, cementing or gluing. It has proved to be particularly advantageous to assemble all the elements of the multi-part mounting part and the post part with a common connecting screw. That is to say the connecting screw braces the occlusal element of the multi-part mounting part with the post part via the screw head or a thread and via a thread in the post part. The remaining elements of the multi-part mounting part are thus braced between the occlusal element of the multi-part mounting part and the post part.

An embodiment example of the invention is explained in more detail below with the aid of drawings. In these.

Figure 6:
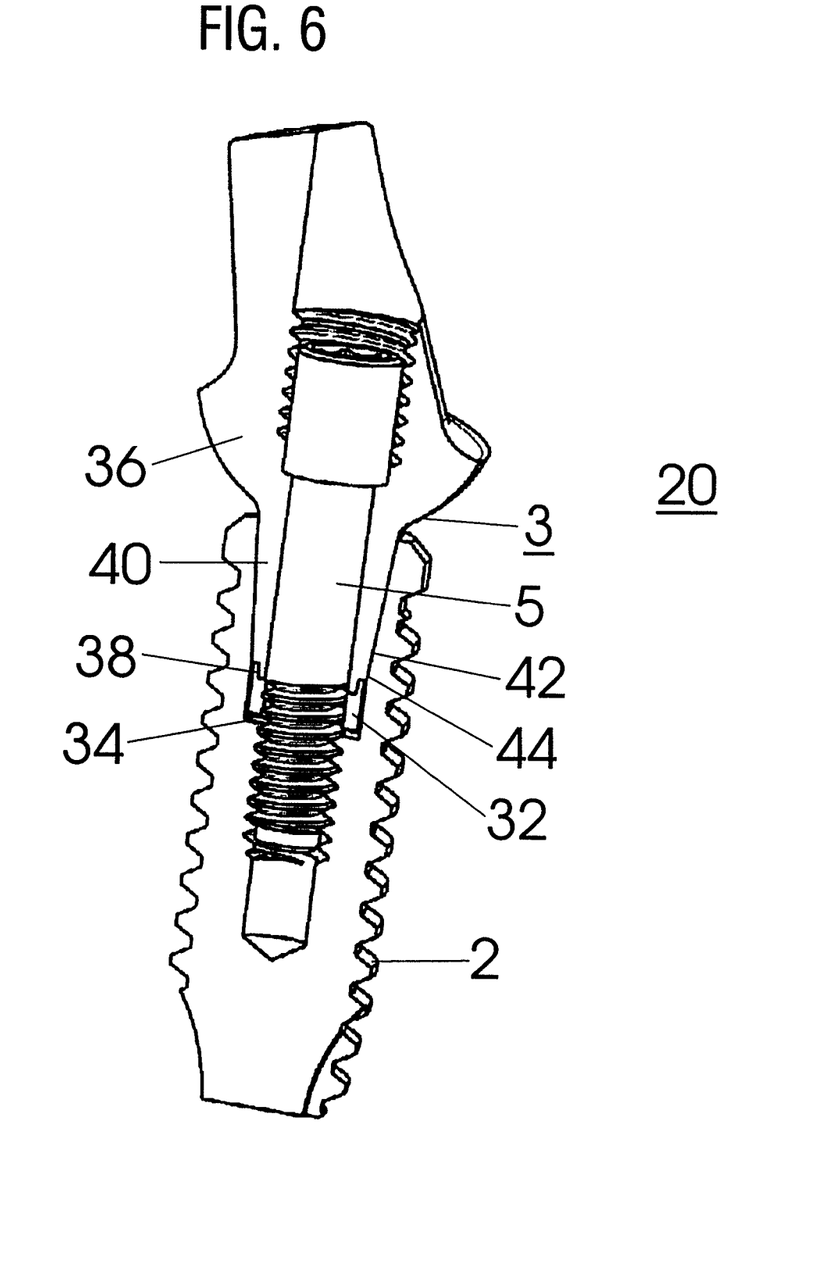
FIG. 6 shows a dental implant according to the invention in longitudinal section, FIG. 7, 8 each show an exploded representation of the dental implant according to FIG. 6, and FIGS. 9A-9E show a number of cross-sections for a receiving channel The same parts have been given the same reference symbols in all the figures.
Figure 7:
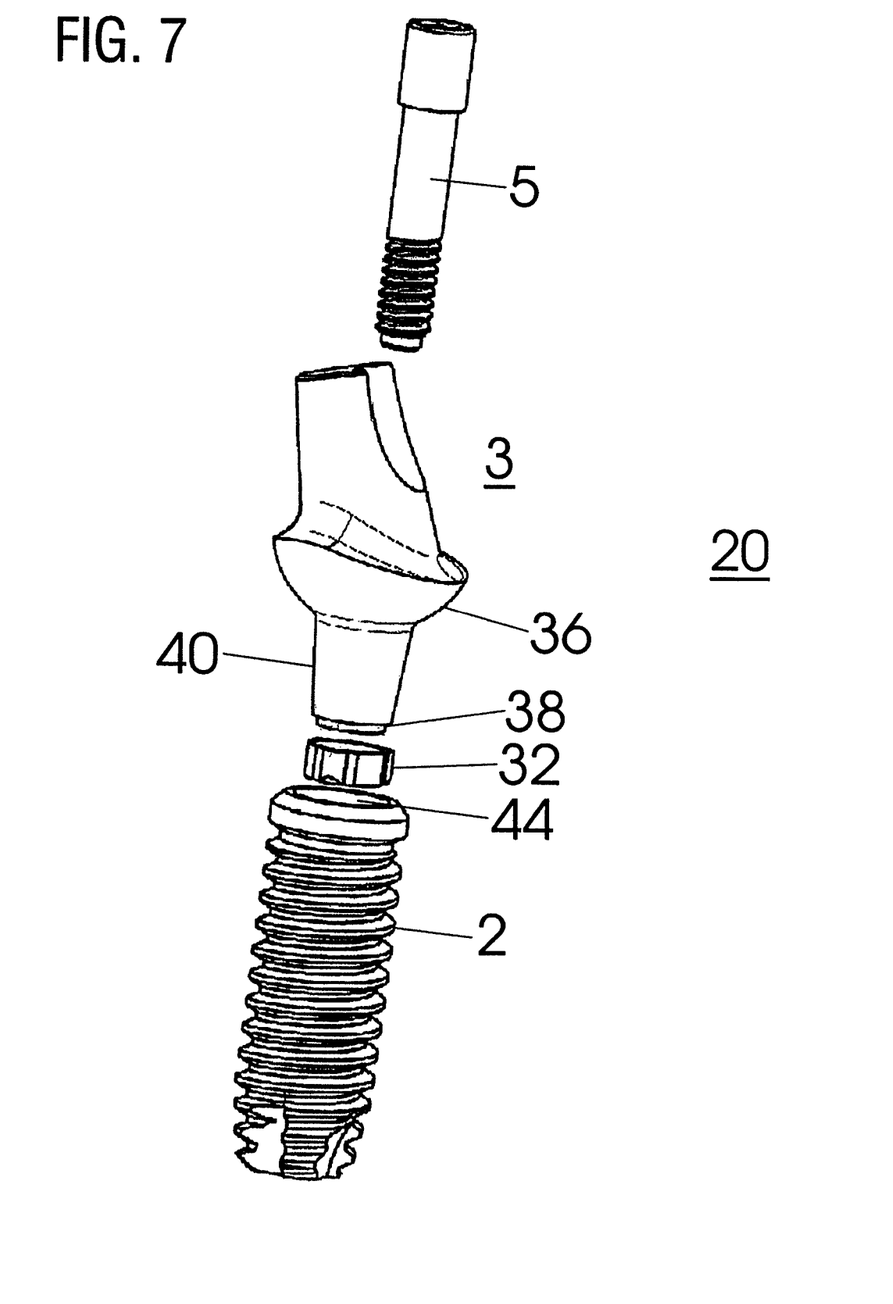
Figure 8:
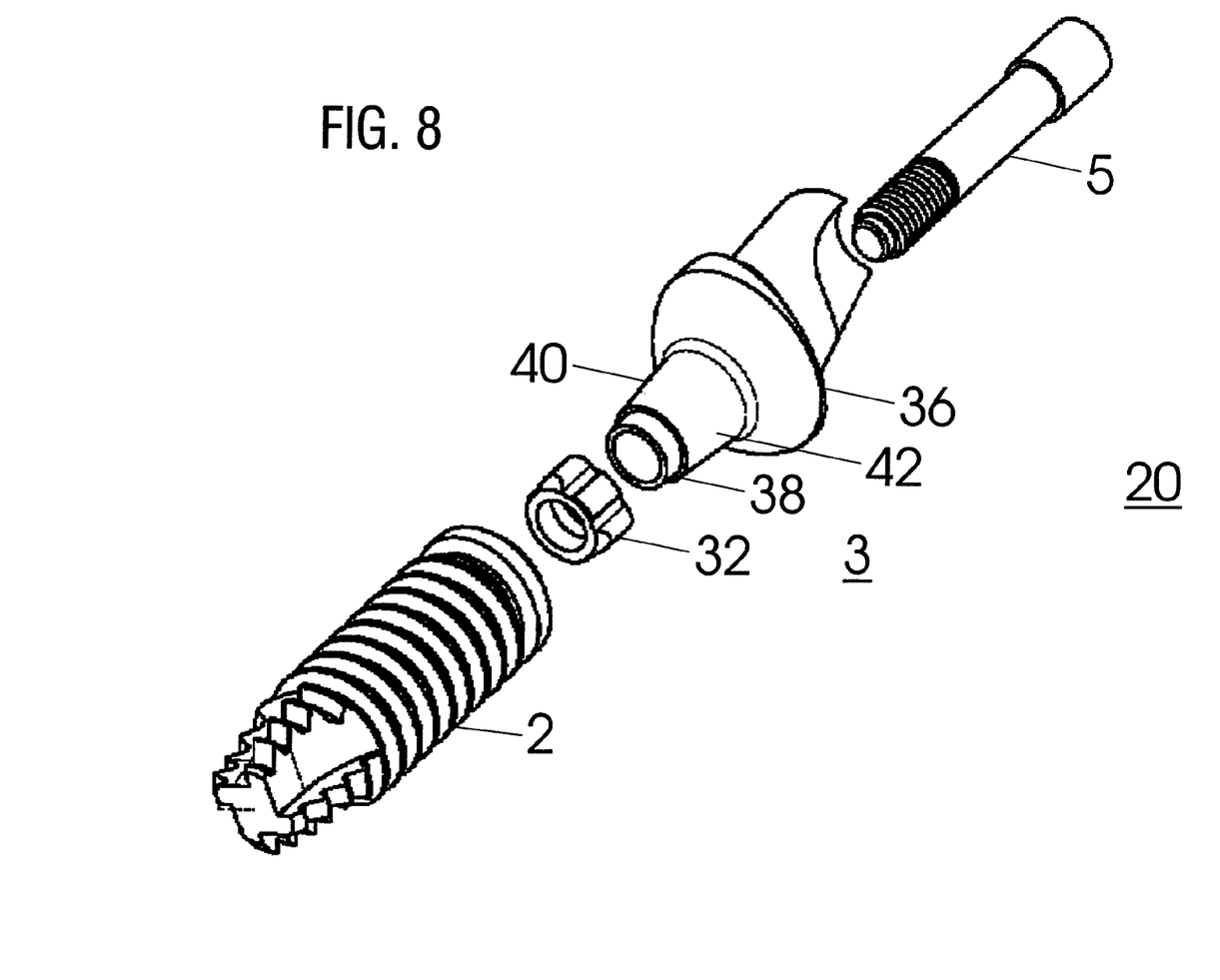
Figure 9A:
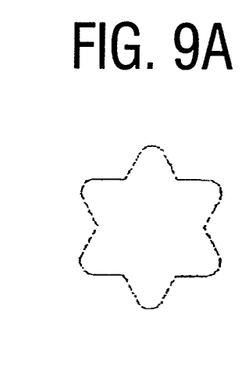
Figure 9B:
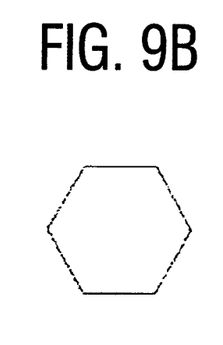
Figure 9C:
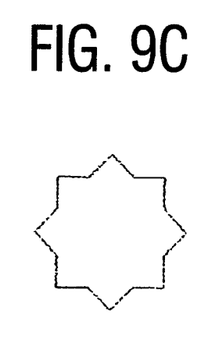
Figure 9D:
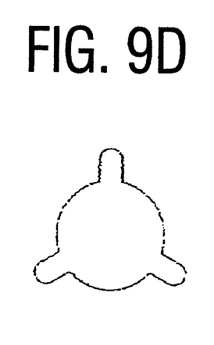
Figure 9E:
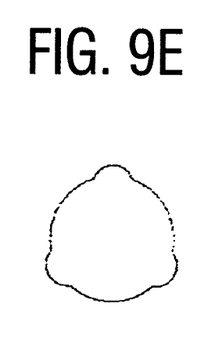

The known dental implants 1 according to FIGS. 1 to 5 each comprise the post part 2 which can be introduced into a jaw bone and a mounting part 3 assigned to this, on to which a dental prosthesis piece can be mounted. In contrast to these known dental implants 1, the dental implant 20 according to the invention according to FIGS. 6 to 8 is designed with the aim that the rotatory positioning of the upper implant structure, in particular the dental prosthesis piece to be mounted, with respect to the longitudinal axis of the post part 2 can indeed in principle be chosen freely, but this can be effected in a first working step outside the patient's mouth and therefore independently of the actual insertion of the implant. The aim here is that a dental technician determines finally in the laboratory, in the manner of a suitable prefabrication, the rotatory adjustment of the upper implant structure depending on the desired orientation taken beforehand from the patient's mouth and therefore aligned as required. In this context, on introduction of the implant into the patient's mouth in the manner of indexing only a small number of positionings are still possible, so that the dentist automatically chooses the correct positioning when integrating the dental prosthesis, and a fine adjustment or the like, requiring outlay, during the treatment in the patient's mouth is therefore not necessary. For this purpose, the mounting part 3 of the dental implant 20 is divided into two, whereby the said decoupling of the working steps is to be achieved by this dividing into two.

For this, the mounting part 3 of the dental implant 20 comprises a first mounting part piece 32 which, viewed in the longitudinal direction of the post part 2, can be pushed into a receiving channel 34. The first mounting part piece 32 is tailored here in its external cross-section to the internal cross-section of the receiving channel 34, the internal contour of the receiving channel 34, like the external contour of the first mounting part piece 32 tailored thereto, having a multi-membered symmetry in cross-section for the desired indexing. It is thus ensured that the first mounting part piece 32 can be pushed into the receiving channel 34 only in a limited number of orientations with respect to the direction it is pushed into the receiving channel 34 or with respect to the longitudinal direction of the post part 2.

In order moreover also to be able to ensure the prestored free rotatory alignment of the upper implant structure, however, the mounting part 3 of the dental implant 20 also has a further second mounting part piece 36 which is intended for assembling the dental prosthesis piece and can be brought into contact with the first mounting part piece 32 in a contact region 38. The contact here should be effected in the manner of a permanent connection in the manner of a preassembling in the laboratory of the dental technician, so that a suitably chosen method which ensures a permanent and firm connection is envisaged for the actual production of the contact. For this, in the embodiment example the first mounting part piece 32 is configured as a clamping ring which can be braced with the second mounting part piece 36 in the contact region 38. The mounting part pieces 32 and 36 provided for formation of the mounting part 3 are designed here with the aim that they can be brought together with freely choosable positioning or orientation... rotary alignment of the second mounting part piece 36 in relation to the indexing given by the external contour of the first mounting part piece 32. For this, the first mounting part piece 32 and the second mounting part piece 36 are each configured with a circular cross-section in the contact region 38, so that the desired bracing or fixing of the two mounting part pieces 32 and 36 with one another can be carried out in any desired orientation relative to one another.

The dental implant 20 moreover is also additionally designed with the aim that in the manner of suitable hermetic sealing, the mechanism formed by the indexing mechanism and the components required for this can be kept free from penetrating bacteria or contamination for permanent use. For this, the second mounting part piece 36 is configured in a corresponding embodiment with the post part 2 such that during final assembling, that is to say when the mounting part 3 composed of the mounting part pieces 32 and 36 is introduced into the post part 2, a bacteria-proof sheathing of the said indexing mechanism is formed in the manner of an encapsulation or covering. For this, the second mounting part piece 36 comprises a peripheral sealing collar 40 with an essentially conical outer surface 42, which can be brought into contact with a corresponding inner surface 44 of the post part 2 to form the capsule surrounding the first mounting part piece 32. As has been found, surprisingly, precisely the conical configuration of the said contact surfaces in fact has the effect that the desired bacteria-proof connection is formed with the mounting part 3 introduced. For final fixing, the second mounting part piece 34 is provided with a screw channel through which the connecting screw 5 is passed for screwing tightly to the post part 2.

In the embodiment example, the internal contour of the receiving channel 34 has a three-membered symmetry in cross-section. For this, the internal contour of the receiving channel 34—like the corresponding external contour of the first mounting part piece 32—is essentially circular in configuration and is complemented by a number of moulded-on cams.

The working steps for introduction of the dental implant 20 can be summarized as follows:

In a first working step, the implant is introduced via a suitable manual or mechanical process known per se. A one-part healing screw is then introduced surgically and the implant is then closed. In a subsequent step, the soft tissue is furthermore shaped surgically for the later intended prosthetic situation.

With this surgical pretreatment in the patient's oral cavity, by resorting to standard methods an impression of the oral or dental situation is produced, on the basis of which the nature, form and alignment of the dental prosthesis piece to be produced can be determined and preset. On this basis, a gypsum model of the dental situation to be produced is produced by a dental technician.

On this basis, the dental implant 20 is prepared in the laboratory by the dental technician, the first mounting part piece 32 configured as a clamping ring on the inside initially being inserted into the receiving channel of a laboratory analogue of the dental implant 20 in the gypsum model already produced. The second mounting part piece 36 is then likewise inserted and suitably aligned with respect to the desired dental situation, no final fixing with the first mounting part piece 32 being carried out yet, but merely a provisional fixing. Resorting to standardized processes based on general dentistry standards, the actual dental prosthesis pieces, that is to say the prostheses, the crowns or the bridges, are then produced and mounted on the second mounting part piece 36. Thereafter, correct and final alignment of the second mounting part piece 36 in relation to the first mounting part piece 32 in the rotatory respect is carried out. A holding screw analogous to the connecting screw 5 is then screwed into an assigned thread in the foundation analogous to the post part 2 in the gypsum model, the second mounting part piece 36 being clamped to the first mounting part piece 32 via the screw head in the axial direction of the screw. Due to the conical configuration of the contact surface 38 of circular cross-section between the first mounting part piece 32 and the second mounting part piece 36, the second mounting part piece 36 is pressed by this means into the first mounting part piece 32 and the first mounting part piece 32 is therefore clamped with the second mounting part piece 36. The self-locking catch of the cone here ensures a definitive fixing of the mounting part pieces 32 and 36 to one another.

The mounting part 3 produced in such a manner by firm connection or clamping of the mounting part pieces 32, 36 to one another, together with the dental prosthesis already mounted thereon, is then detached from the gypsum model. In a subsequent treatment step, the mounting part 3 is then introduced into the patient's mouth by pushing in and connecting with the post part 2 already present. Due to the indexing or prepositioning effected by the first mounting part piece 32, fine adjustment, requiring outlay, of the rotatory orientation during the treatment in the patient's mouth can be omitted here.

A number of possibly suitable cross-section geometries for the receiving channel 34 and the corresponding external contour of the first mounting part piece 32 configured as a clamping ring are shown in FIG. 9. In particular, it can be seen here from the embodiment according to FIG. 9 *d*) or 9 *e*) that this contour can be essentially circular filled with a number of moulded-on cams.

LIST OF REFERENCE SYMBOLS

1 Dental implant
2 Post part
3 Mounting part
5 Connecting screw
20 Dental implant
32 First Mounting part piece
34 Receiving channel
36 Second Mounting part piece
38 Contact region
40 Sealing collar
42 Conical outer surface

The invention claimed is:

1. A dental implant system having
a post part which is configured to be introduced into a jaw bone;
a mounting part configured to mount a dental prosthesis piece, said mounting part comprises
a first mounting part piece which, viewed in the longitudinal direction of the post part, is configured to be inserted into a receiving channel in the post part, and
a second mounting part piece on which the dental prosthesis piece is to be mounted,
wherein the second mounting part piece is configured to be brought into contact with the first mounting part piece in a contact region, said contact region having an essentially circular cross-section such that, while in contact with the first mounting part piece, the second mounting part piece is capable of freely rotating about its longitudinal axis until being immovably fixed with the first mounting part piece,
wherein an internal contour of the receiving channel in the post part corresponds to an external contour of the first mounting part piece, and has a one- or multi-fold symmetry in cross-section that fixes the first mounting part piece against rotation, and
wherein the second mounting part piece has a peripheral sealing collar having an essentially conical and tapered outer surface which is configured to be brought into contact with an inner surface of the post part, said inner surface having an internal contour corresponding to the outer surface of the peripheral sealing collar, to form a capsule surrounding the first mounting part piece.

2. The dental implant system according to claim 1, wherein the inner surface of the post part has a conical and tapered configuration.

3. The dental implant system according to claim 1, wherein the internal contour of the receiving channel has a three-membered symmetry in cross-section.

4. The dental implant system according to claim 1, wherein the internal contour of the receiving channel has essentially a polygonal configuration in cross-section.

5. The dental implant system according to claim 1, wherein the internal contour of the receiving channel is essentially circular in cross-section, complemented by a number of moulded-on cams.

6. The dental implant system according to claim 1, wherein the first mounting part piece is configured as a clamping ring which is configured to be braced with the second mounting part piece in the contact region.

7. A method for providing a mounting part of a dental implant system according to claim 1 for introduction into a patient's mouth, which comprises securely fixing the first mounting part piece against twisting on the second mounting part piece before the second mounting part piece is inserted into the post part.

* * * * *